(12) United States Patent
Bruening et al.

(10) Patent No.: US 8,765,104 B2
(45) Date of Patent: Jul. 1, 2014

(54) DEODORIZING PREPARATIONS

(75) Inventors: Stefan Bruening, Duesseldorf (DE);
Helga Gondek, Duesseldorf (DE);
Achim Ansmann, Erkrath (DE)

(73) Assignee: Cognis IP Management GmbH, Duesseldorf (DE)

( * ) Notice: Subject to any disclaimer, the term of this patent is extended or adjusted under 35 U.S.C. 154(b) by 643 days.

(21) Appl. No.: 12/202,990

(22) Filed: Sep. 2, 2008

(65) Prior Publication Data
US 2008/0317694 A1   Dec. 25, 2008

Related U.S. Application Data

(63) Continuation of application No. 10/181,641, filed as application No. PCT/EP01/00321 on Jan. 12, 2001, now abandoned.

(30) Foreign Application Priority Data

Jan. 21, 2000 (DE) .................... 100 02 643

(51) Int. Cl.
*A61K 8/00* (2006.01)
*A61K 8/28* (2006.01)

(52) U.S. Cl.
USPC .................. 424/65; 424/66; 424/67; 424/68; 424/401

(58) Field of Classification Search
USPC .......... 424/65, 66, 67, 68, 401, 76.1
See application file for complete search history.

(56) References Cited

U.S. PATENT DOCUMENTS 5,968,488 A   10/1999   Wachter et al.
6,045,785 A    4/2000   Wachter et al.

FOREIGN PATENT DOCUMENTS

| JP | 11106326 | 4/1999 |
| JP | 11246378 | 9/1999 |
| JP | 2000016928 | 1/2000 |
| WO | 95/16824 | 6/1995 |
| WO | 95/35412 | 12/1995 |
| WO | 95/35441 | 12/1995 |
| WO | 96/24723 | 8/1996 |
| WO | 97/16164 | 5/1997 |
| WO | 97/46205 | 12/1997 |
| WO | 97/47282 | 12/1997 |
| WO | 98/17241 | 4/1998 |
| WO | 01/22933 | 4/2001 |

*Primary Examiner* — Sreeni Padmanabhan
*Assistant Examiner* — Shobha Kantamneni
(74) *Attorney, Agent, or Firm* — Servilla Whitney LLC

(57) ABSTRACT

A deodorizing composition containing: (a) from about 10 to 30% by weight of a dialkyl carbonate corresponding to formula I:

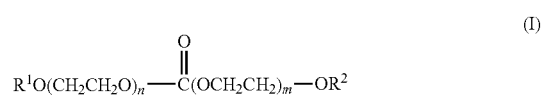

wherein $R^1$ is a linear alkyl and/or alkenyl group containing from about 6 to 22 carbon atoms, a 2-ethylhexyl, an isotridecyl, an isostearyl group or a group derived from a polyol containing 2 to 15 carbon atoms and at least two hydroxyl groups; $R^2$ has the same meaning as $R^1$ or is an alkyl group containing from about 1 to 5 carbon atoms; and n and m, independently of one another, represent a number up to 100, and (b) an antiperspirant.

5 Claims, No Drawings

DEODORIZING PREPARATIONS

CROSS REFERENCE

This application is a continuation of U.S. National Stage application Ser. No. 10/181,641 filed Jul. 19, 2002 which claims priority to PCT/EP01/00321, filed Jan. 12, 2001, which claims priority to German Appln. No. 100 02 643.5, filed Jan. 21, 2000, each of which is herein incorporated by reference.

FIELD OF THE INVENTION

This invention relates to deodorizing preparations containing dialkyl carbonates, antiperspirants, esterase inhibitors, bactericidal or bacteriostatic agents and/or perspiration-absorbing substances and to their use for the production of deodorizing preparations.

BACKGROUND OF THE INVENTION

In the field of personal care, deodorants are used to eliminate unpleasant body odors. Examples of such substances are aluminium compounds, such as aluminium sulfate or aluminium chlorhydrate, zinc salts and citric acid compounds. Since the problem of odor inhibition has by no means been completely solved, there is still a need for new preparations in which the deodorants can readily be emulsified and incorporated. This is intended to ensure more uniform distribution of the deodorants and, hence, an improvement in their effect, i.e. minimization of perspiration and a reduction in odor formation. In addition, the feeling of the skin after the application of deodorants should be improved and greater stability of the final formulations achieved in relation to the prior art.

Accordingly, the problem addressed by the invention was to provide such products.

DESCRIPTION OF THE INVENTION

The present invention relates to deodorizing preparations containing
(a) dialkyl carbonates corresponding to formula (I):

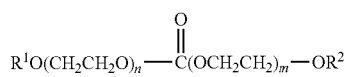

(I)

in which $R^1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R^2$ has the same meaning as $R^1$ or is an alkyl group containing 1 to 5 carbon atoms and n and m independently of one another stand for 0 or numbers of 1 to 100,
(b1) antiperspirants,
(b2) esterase inhibitors,
(b3) bactericidal or bacteriostatic agents and/or
(b4) perspiration-absorbing substances.

The use of antiperspirants, esterase inhibitors (for example triethyl citrate), bactericidal agents (for example chitosan) and/or perspiration-absorbing substances for the production of deodorizing and/or perspiration-inhibiting compositions is known from the prior art. It has surprisingly been found that the emulsification properties of deodorizing preparations of the substances mentioned above can be significantly improved by dialkyl carbonates. Of particular advantage is the more homogeneous distribution of the deodorants where dialkyl carbonate is present which leads to an improvement in the effect and hence to a minimization of perspiration and a reduction in odor formation. In addition, the feeling on the skin in terms of smoothness, powderiness, absorption behavior and dryness is improved. The greater stability of the final formulations has proved to be another advantage. In the case of suspension sticks and "suspension soft solids", transparent application ("rub-off") is facilitated.

Dialkyl Carbonates

Dialkyl carbonates which form component (a) are basically known compounds even through some of the claimed compounds are being described for the first time in the present specification. Basically, they may be prepared by transesterification of dimethyl or diethyl carbonate with the hydroxy compounds mentioned using known methods. A review of these methods can be found, for example, in Chem. Rev. 96, 951 (1996). Dialkyl carbonates corresponding to formula (I) which are particularly suitable for solving the stated problem satisfy one of the following requirements:
(A) $R^1$ is a linear alkyl group containing 8 to 18 carbon atoms or a 2-ethylhexyl group and $R^2$ has the same meaning as $R^1$ or represents methyl;
(B) $R^1$ is a linear alkyl group containing 12 to 18 carbon atoms, $R^2$ has the same meaning as $R^1$ or represents methyl and n and m stand for numbers of 1 to 10;
(C) $R^1$ is a residue of a polyol selected from the group consisting of glycerol, alkylene glycols, technical oligoglycerol mixtures, methylol compounds, lower alkyl glucosides, sugar alcohols, sugars and aminosugars and $R^2$ has the same meaning as $R^1$ or represents a linear or branched alkyl group containing 8 to 12 carbon atoms or methyl.

Typical examples of dialkyl carbonates belonging to the two groups (A) and (B) are complete or partial transesterification products of dimethyl and/or diethyl carbonate with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof formed, for example, in the high-pressure hydrogenation of technical methyl esters based on fats and oils or aldehydes from Roelen's oxosynthesis and as monomer fraction in the dimerization of unsaturated fatty alcohols. The transesterification products of the lower carbonates with the alcohols mentioned in the form of their adducts with 1 to 100, preferably 2 to 50 and more preferably 5 to 20 moles of ethylene oxide are also suitable. Di-n-octyl carbonates are preferred The carbonates of group (C) are being described for the first time in the present specification. They are compounds which are obtained by complete or partial transesterification of dimethyl and/or diethyl carbonate with polyols. Polyols suitable for the purposes of the invention preferably contain 2 to 15 carbon atoms and at least two hydroxyl groups. Typical examples are
glycerol;
alkylene glycols such as, for example, ethylene glycol, diethylene glycol, propylene glycol, butylene glycol, hexylene glycol and also polyethylene glycols with an average molecular weight of 100 to 1,000 dalton;

technical oligoglycerol mixtures with a degree of self-condensation of 1.5 to 10, for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, more particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

This reaction can of course not only result in replacement of a methyl or ethyl group by a polyol residue, it also gives a mixture in which several hydroxy groups or even all the hydroxyl groups of the polyol are attached to carbonate groups so that an oligomeric or polymeric net structure may even be obtained. In the context of the invention, compounds of this type are also meant to fall within the scope of general formula (I).

The preparations according to the invention may contain the dialkyl carbonates in quantities of 1 to 80, preferably 5 to 50 and more particularly 10 to 30% by weight, based on the solids content.

Antiperspirants

The antiperspirants of component (b1) are salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Aluminium chlorohydrate, aluminium zirconium tetrachlorohydrate, aluminium zirconium pentachlorohydrate and complex compounds thereof are preferably used. In addition, antiperspirants may contain typical oil-soluble and water-soluble auxiliaries in relatively small amounts. Oil-soluble auxiliaries such as these include, for example, inflammation-inhibiting, skin-protecting or pleasant-smelling essential oils, synthetic skin-protecting agents and/or oil-soluble perfume oils.

The preparations according to the invention may contain the antiperspirants in quantities of 1 to 50, preferably 5 to 30 and more particularly 10 to 25% by weight, based on the solids content.

Esterase Inhibitors

Where perspiration is present in the underarm region, extracellular enzymes—esterases, mainly proteases and/or lipases—are formed by bacteria and split the esters present in the perspiration, releasing odors in the process. Esterase inhibitors of component (b2) are preferably trialkyl citrates, such as trimethyl citrate, tripropyl citrate, triisopropyl citrate, tributyl citrate and, in particular, triethyl citrate (Hydagen® CAT, Cognis GmbH, Dusseldorf, FRG). Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

The preparations according to the invention may contain the esterase inhibitors in quantities of 0.01 to 20, preferably 0.1 to 10 and more particularly 0.5 to 5% by weight, based on the solids content.

Bactericidal or Bacteriostatic Agents

Typical examples of suitable bactericidal or bacteriostatic agents of component (b3) are, in particular, chitosan and phenoxyethanol. 5-Chloro-2-(2,4-dichlorophenoxy)-phenol which is marketed under the name of Irgasan® by Ciba-Geigy, Basle, Switzerland, has proved to be particularly effective.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GM L), diglycerol monocaprate (DMC), salicylic acid-N-alkylamides such as, for example, salicylic acid-n-octyl amide or salicylic acid-n-decyl amide.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat.

The preparations according to the invention may contain the bactericidal or bacteriostatic agents in quantities of 0.01 to 5% by weight and preferably 0.1 to 2% by weight, based on the solids content.

Perspiration-absorbing Substances

Suitable perspiration absorbers which form component (b4) are modified starch such as, for example, Dry Flo Plus (National Starch), silicates, talcum and other substances of similar modification which appear suitable for absorbing perspiration.

The preparations according to the invention may contain the perspiration-absorbing substances in quantities of 0.1 to 30% by weight, preferably 1 to 20% by weight and more particularly 5 to 10% by weight, based on the solids content.

Commercial Applications

The present invention also relates to the use of preparations of dialkyl carbonates, antiperspirants, UV filters, esterase inhibitors, bactericidal or bacteriostatic agents and/or perspiration absorbers for the production of deodorizing preparations.

In a preferred embodiment of the invention, the compositions may contain components (a) and (b) in preferably the following quantities, based on the solids content:
(a) 1 to 80, preferably 5 to 50 and more particularly 10 to 30% by weight of dialkyl carbonates,
(b) 1 to 50 and preferably 5 to 25% by weight of antiperspirants,
(c) 0.01 to 20 and preferably 1 to 5% by weight of esterase inhibitors,
(d) 0.01 to 5 and preferably 0.1 to 1% by weight of bactericidal or bacteriostatic agents and/or
(e) 0.1 to 30 and preferably 1 to 20% by weight of perspiration absorbers,
expressed as the active substance content of the components, with the proviso that the quantities shown add up to 100% by weight with water and other auxiliaries and additives.

Auxiliaries and Additives

In order to be able to apply the active components to the skin in a measurable, economical, convenient and cosmetically attractive manner, they are normally incorporated in formulation bases (for typical ingredients, see below). The most important bases include alcoholic and aqueous/alcoholic solutions, emulsions, gels, oils, wax/fat compounds, stick preparations and powders. Other ingredients are superfatting agents, emulsifiers, antioxidants and perfume oils, essential oils, dyes and—for spray applications—propellent gases, such as propane and/or butane for example. The preparations are preferably marketed as rollers (roll-on emulsions), sticks, deodorant or pump sprays.

These preparations may contain mild surfactants, pearlizing waxes, consistency factors, thickeners, stabilizers, polymers, silicone compounds, fats, waxes, lecithins, phospholipids, biogenic agents, additional deodorants, film formers, solubilizers, preservatives, dyes and the like as further auxiliaries and additives.

Surfactants

Suitable surfactants are anionic, nonionic, cationic and/or amphoteric or zwitterionic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide(ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes.

Emulsifiers

Suitable emulsifiers are, for example, nonionic surfactants from at least one of the following groups:

products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group;

alkyl and/or alkenyl oligoglycosides containing 8 to 22 carbon atoms in the alkyl group and ethoxylated analogs thereof;

adducts of 1 to 15 moles of ethylene oxide with castor oil and/or hydrogenated castor oil;

adducts of 15 to 60 moles of ethylene oxide with castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 moles of ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 moles of ethylene oxide;

mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethylene glycol-30 Dipolyhydroxystearate;

polymer emulsifiers, for example Pemulen types (TR-1, TR-2) of Goodrich;

polyalkylene glycols and glycerol carbonate.

The addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE 20 24 051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 moles of ethylene oxide with the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Poly-glyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 moles of ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs) and correspond to the following general formula:

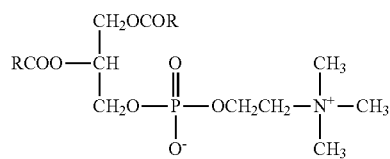

where R typically represents linear aliphatic hydrocarbon radicals containing 15 to 17 carbon atoms and up to 4 cis-double bonds. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlescing Waxes

Suitable pearlescing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grunau), quaternized wheat polypeptides, polyethyleneimine, cationic silicone polymers such as, for example, Amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosmetics & Toiletries, Vol. 108, May 1993, pages 95 et seq.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Biogenic Agents

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomethyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione and the enamine compounds described in DE 197 12 033 A1 (BASF). The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or dimethicones. So-called micro- or nanopigments are preferably used in sun protection products. Micronized zinc oxide is preferably used. Other suitable UV filters can be found in P. Finkel's review in SÖFW-Journal 122, 543 (1996) and in Parfümerie und Kosmetik 3 (1999), pages 11 et seq.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Perfume Oils

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, p-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

EXAMPLES

TABLE 1

| Antiperspirant suspension sticks and soft solids - quantities = % by weight | | | | | | |
|---|---|---|---|---|---|---|
| Composition | 1 | 2 | 3 | 4 | 5 | 6 |
| 12-Hydroxy-stearic acid | — | — | — | — | — | — |
| Distearyl ether | — | 15 | — | — | — | — |
| Stearyl alcohol | — | — | 10 | 10 | 14.7 | — |
| Guerbet alcohol C36 | 15 | — | — | — | — | — |
| Tribehenin | — | — | — | — | — | 20 |
| Hyrogenated Castor Oil | — | — | — | — | 3.7 | — |
| Dioctyl carbonate | 20 | 60 | 60 | 60 | 58.7 | 55 |
| Octyl dodecanol | 10 | — | — | — | — | — |
| Dicaprylyl ether | 10 | — | — | — | — | — |
| Hexyl decanol + Hexyldecyl Laurate | 10 | — | — | — | — | — |
| Cyclomethicone | 10 | — | — | — | — | — |
| Dry Flo Plus* | — | — | 5 | — | — | — |
| Silica | — | — | — | 2.5 | — | — |
| Talcum | — | — | — | 2.5 | — | — |
| Aluminium Zirconium Tetrachlorohydrex GLY | — | — | 25 | 25 | 22.9 | 25 |
| Aluminium Chlorohydrate | 25 | 25 | — | — | — | — |
| Rub-off color | White | White | White | White | White | White |
| Hardness** | 4.2 | 4.2 | 5.0 | 4.9 | 4.2 | 4.6 |
| Oil secretion | No | No | No | No | No | No |
| Feeling on the skin | Particularly velvety, soft, powdery, dry | Particularly velvety, soft, powdery, dry | Particularly velvety, soft, powdery, particularly dry, not oily at beginning | Particularly velvety, soft, powdery, particularly dry | Particularly velvety, soft, powdery, dry | Soft, creamy, powdery |

| Antiperspirant suspension sticks and soft solids - quantities in % by weight | | | | |
|---|---|---|---|---|
| Composition | 7 | 8 | 9 | 10 |
| 12-Hydroxystearic acid | 10 | 5 | — | 10 |
| Distearyl ether | — | — | — | — |
| Stearyl alcohol | — | — | 18 | — |
| Tribehenin | — | — | — | — |
| Hydrogenated Castor Oil | — | — | 5 | — |
| Dioctyl Carbonate | 65 | 65 | — | — |
| Octyl dodecanol | — | — | 15 | 15 |
| Cyclomethicone | — | — | 37 | 50 |
| Dry Flo Plus* | — | 5 | — | — |
| Silica | — | — | — | — |
| Talcum | — | — | — | — |
| Aluminium Zirconium Tetrachlorohydrex GLY | 25 | 25 | — | 25 |
| Aluminium Chlorohydrate | — | — | 25 | — |
| Rub-off color | Transparent | Transparent | Transparent | Transparent |
| Hardness** | 4.0 | 5.0 | 4.1 | 4.0 |
| Oil secretion | No | No | No | No |

TABLE 1-continued

| Antiperspirant suspension sticks and soft solids - quantities = % by weight | | | | |
|---|---|---|---|---|
| Feeling on the skin | Particularly velvety, soft, powdery, dry | Particularly velvety, soft, powdery, particularly dry, not oily at beginning | Wax-like, dry | Soft, slightly powdery |

*National Starch
**As measured with a Penetrometer PNR 10 Petrotest

The emulsification properties and stability of the preparations according to the invention were subjectively evaluated (+=very good, −=satisfactory). Compositions 1 to 4 correspond to the invention, formulation C1 is intended for comparison.

TABLE 2

| Antiperspirant/deodorant creams - quantities in % by weight | | | | | |
|---|---|---|---|---|---|
| Composition | 1 | 2 | 3 | 4 | C1 |
| Emulgade SE-PF* | 6.0 | 6.0 | 6.0 | 6.0 | 6.0 |
| Sodium Cetearyl Sulfate | 0.5 | 0.5 | 0.5 | 0.5 | 0.5 |
| Cetearyl alcohol | 1 | 1 | – | – | 2 |
| Behenyl alcohol | 3 | 3 | 4 | 4 | 2 |
| Dioctyl carbonate | 6.0 | 3 | 9.0 | 9.0 | – |
| Cyclomethicone | 3.0 | 2 | – | – | – |
| Octyl dodecanol | – | 1 | – | – | – |
| Dicaprylyl ether | – | 2 | – | – | – |
| Hexyldecanol + Hexyldecyl Laurate | – | 1 | – | – | – |
| Dioctyl cyclohexane | – | – | – | – | 9.0 |
| Farnesol | – | – | – | 0.2 | – |
| Triethyl citrate | – | – | – | 1.5 | – |
| Talcum | 10.0 | 10.0 | 10.0 | 10.0 | 10.0 |
| Chitosan | – | – | 0.1 | – | – |
| Glycolic acid | – | – | 0.04 | – | – |
| Aluminium Zirconium Tetrachlorohydrex GLY | 15.0 | 15.0 | 10.0 | 10.0 | 15.0 |
| Water, demin. | to | to | to | to | to |
| Viscosity** | 390,000 | 390,000 | 400,000 | 400,000 | 400,000 |
| Emulsification properties | + | + | + | + | – |
| Homogeneous distribution of active principle | + | + | + | + | – |
| Stability | + | + | + | + | – |
| Feeling on the skin | Very velvety, soft | Very velvety, soft | Particularly velvety, soft, powdery and caring | Very velvety, soft | Not very velvety or soft |

*COGNIS,
**Brookfield, RVF, 23° C., spindle TE, mPas, rpm 4 Helipath

The emulsification properties and stability of the preparations according to the invention were subjectively evaluated (+=very good, −=satisfactory). Compositions 1 to 4 correspond to the invention, formulations C1 and C2 are intended for comparison. The results are set out in Table 3.

TABLE 3

| Oil-in-water emulsions for roll-on and sprayable antiperspirant/deodorant applications - quantities in % by weight | | | | | | |
|---|---|---|---|---|---|---|
| Composition | 1 | 2 | C1 | 3 | 4 | C2 |
| Emulgade SE-PF* | 4.1 | 4.1 | 4.1 | – | – | – |
| Ceteareth-20 | 09 | 0.9 | 0.9 | 1.5 | 1.5 | 1.5 |
| Ceteareth-10 | – | – | – | 1.5 | 1.5 | 1.5 |

TABLE 3-continued

Oil-in-water emulsions for roll-on and sprayable antiperspirant/deodorant applications - quantities in % by weight

| Composition | 1 | 2 | C1 | 3 | 4 | C2 |
|---|---|---|---|---|---|---|
| Glyceryl Stearate | – | – | – | 5.0 | 5.0 | 5.0 |
| Cetyl Alcohol | – | – | – | 3.0 | 3.0 | 3.0 |
| Octyl dodecanol | – | – | – | – | – | 1.5 |
| Decyl Oleate | – | – | – | – | – | 1.5 |
| Dioctyl carbonate | 10.0 | 3 | – | 3.0 | 3.0 | – |
| Cyclomethicone | – | 2 | – | – | – | – |
| Octyl dodecanol | – | 2 | – | – | – | – |
| Dicaprylyl ether | – | 2 | – | – | – | – |
| Hexyl decanol + Hexyldecyl Laurate | – | 1 | – | – | – | – |
| Coco-Caprylate/Caprate | – | – | 10.0 | – | – | – |
| Triethyl citrate | – | – | 1.0 | – | 0.5 | – |
| Irgasan DP 300 | – | – | 0.2 | – | – | – |
| Chitosan | 0.1 | 0.1 | – | – | 0.1 | – |
| Glycolic acid | 0.04 | 0.04 | – | – | 0.04 | – |
| Aluminium Zirconium Tetrachlorohydrex GLY | 15.0 | 15.0 | – | – | – | – |
| Aluminium Chlorohydrate | – | – | 10.0 | 10.0 | 5.0 | 10.0 |
| Water, demin. | to | to | to | to | to | to |
| Viscosity** | <100 | <100 | <100 | 3,000 | 3,000 | 3,000 |
| Emulsification properties | + | + | – | + | + | – |
| Stability | + | + | – | + | + | – |
| Feeling on the skin | Quickly absorbed, fairly dry caring skin feel | Quickly absorbed, fairly dry caring skin feel | Less caring, less dry skin feel | Quickly absorbed, fairly dry caring skin feel | Quickly absorbed, fairly dry caring skin feel | Less caring, less dry skin feel |

*COGNIS,
**Brookfield, RVF, 23° C., spindle 4, mPas, n.d. = not determined

The invention claimed is:

1. A process for inhibiting skin from emanating an unpleasant odor, comprising contacting the skin with a suspension stick or soft solid deodorizing composition consisting essentially of:
   (a) from 30 to 65% by weight, based on a solids content of the composition, of di-n-octyl carbonate;
   (b) from 1% to 50% by weight, based on a solids content, of an antiperspirant;
   (c) from 0.01% to 20% by weight, based on a solids content, of an esterase inhibitor;
   (d) from 0.01% to 5% by weight, based on a solids content, of a bactericidal agent and/or bacteriostatic agent; and
   (e) from 0.1% to 30% by weight, based on a solids content, of a perspiration absorber.

2. A suspension stick or soft solid deodorizing composition consisting essentially of:
   (a) from 30 to 65% by weight of di-n-octyl carbonate,
   (b) from about 0.01% to about 5% by weight of at least one bactericidal and/or bacteriostatic agent,
   (c) from about 1% to about 50% by weight of one or more antiperspirants,
   (d) from about 0.1% to about 30% by weight of one or more perspiration absorbers,
   (e) from about 0.01% to about 20% by weight of esterase inhibitors, and
   (f) remainder, to 100% by weight, of water, auxiliaries and/or additives, said weight percentages being based on the total weight of solids in the composition.

3. A method of deodorizing comprising applying a deodorizing composition according to claim 2.

4. The composition of claim 1 wherein said antiperspirant comprises a member selected from the group consisting of salts of aluminum, zirconium, zinc, and mixtures thereof.

5. The process of claim 1 wherein the antiperspirant comprises a member selected from the group consisting of salts of aluminum, zirconium, zinc, and mixtures thereof.

* * * * *

UNITED STATES PATENT AND TRADEMARK OFFICE
CERTIFICATE OF CORRECTION

PATENT NO. : 8,765,104 B2
APPLICATION NO. : 12/202990
DATED : July 1, 2014
INVENTOR(S) : Stefan Bruening, Helga Gondek and Achim Ansmann Page 1 of 1

It is certified that error appears in the above-identified patent and that said Letters Patent is hereby corrected as shown below:

In the Claims

In claim 4, column 20, line 49: "The composition of claim 1" should be changed to --The composition of claim 2--.

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,765,104 B2 | Page 1 of 1 |
| APPLICATION NO. | : 12/202990 | |
| DATED | : July 1, 2014 | |
| INVENTOR(S) | : Bruening et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 687 days.

Signed and Sealed this
Twenty-first Day of July, 2015

Michelle K. Lee
*Director of the United States Patent and Trademark Office*